United States Patent [19]

Okuhara et al.

[11] Patent Number: 4,939,241
[45] Date of Patent: Jul. 3, 1990

[54] AMINO ACID DERIVATIVES OF ANTITUMOR ACTIVITY

[75] Inventors: Masakuni Okuhara; Toshio Goto; Masami Ezaki; Miho Tanaka; Shigehiro Takase; Hidenori Nakajima; Hideo Hirai; Akira Katayama, all of Tsukuba, Japan

[73] Assignee: Fujisawa Pharmaceutical Co., Ltd., Osaka, Japan

[21] Appl. No.: 173,294

[22] Filed: Mar. 25, 1988

[30] Foreign Application Priority Data

Mar. 30, 1987 [GB] United Kingdom ................ 8707515

[51] Int. Cl.$^5$ ................ C07C 245/12; C07C 245/18; A61K 31/655
[52] U.S. Cl. .................................. 534/556; 534/558; 534/565; 435/116; 435/886; 548/419; 560/155; 560/169; 560/171; 560/172; 514/15
[58] Field of Search ................ 534/556, 565, 562

[56] References Cited

U.S. PATENT DOCUMENTS

| | | | |
|---|---|---|---|
| 2,490,714 | 12/1949 | Searle | 534/556 |
| 2,691,649 | 10/1954 | Hammond | 534/556 |
| 2,691,650 | 10/1954 | Hammond | 534/556 |
| 3,226,381 | 12/1965 | Breslow et al. | 534/556 X |

OTHER PUBLICATIONS

"New Agent Data Summaries", Cancer Chemotherapy Reports, No. 7: 65–86, 1960.
Birkofer, BBR, Deut. Chem. Gesell, vol. 85, pp. 83 to 94 (1947).
Fahr et al, Chemical Abstracts, vol. 62, cols. 14540 to 14541 (1965).
Hoermann et al, Chemical Abstracts, vol. 59, 3438a–d (1963).
"Merck Index", Tenth Edition, p. 130 (1983).
Perold, Chemical Abstracts, vol. 50, 6326d to 6327a (1956).
Regitz et al, Chemical Abstracts, vol. 69, 67056r (1968).
Regitz et al, Chemical Abstracts vol. 71, 60640j (1969).
Schoellkopf et al, Chemical Abstracts, vol. 82, 155228x (1975).
Wenkert et al, J. Amer. Chem. Soc., vol. 94, No. 23, pp. 8084 to 8090 (1972).

*Primary Examiner*—Floyd D. Higel
*Attorney, Agent, or Firm*—Oblon, Spivak, McCelland, Maier & Neustadt

[57] ABSTRACT

The invention relates to compounds of antitumor activity of the formula:

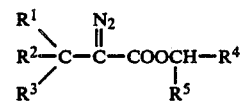

ps in which
$R^1$ is hydrogen, lower allkyl, halo(lower)alkyl or aryl,
$R^2$ is hydrogen, hydroxy or protected hydroxy,
$R^3$ is hydrogen,
$R^4$ is aminocarboxy(lower)alkyl, protected amino(lower)alkyl or protected aminocarboxy(lower)alkyl, and
$R^5$ is hydrogen or lower alkyl, or its pharmaceutical acceptable salt.

1 Claim, No Drawings

AMINO ACID DERIVATIVES OF ANTITUMOR ACTIVITY

This invention relates to new amino acid derivatives. More particularly, this invention relates to amino acid derivatives and their pharmaceutically acceptable salts which have an anti-tumor activity, to processes for their preparation and to pharmaceutical compositions comprising the same.

The amino acid derivatives can be represented by the following formula:

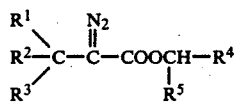

in which
 $R^1$ is hydrogen, lower alkyl, halo(lower)alkyl or aryl
 $R^2$ is hydrogen, hydroxy or protected hydroxy,
 $R^3$ is hydrogen,
 $R^4$ is a lower alkyl, amino(lower)alkyl, carboxy(lower)alkyl, aminocarboxy(lower)alkyl protected amino(lower)alkyl or protected amino-carboxy(lower)alkyl, and
 $R^5$ is hydrogen or lower alkyl; or
 $R^2$ and $R^3$ may combine to be oxo, and
 $R^1$, $R^4$ and $R^5$ are the same as defined above.

According to the present invention, the amino acid derivatives (I) and their pharmaceutically acceptable salts can be prepared by the following processes. (1) Chemical synthesis:

Process 1

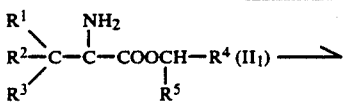

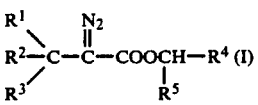

Process 2

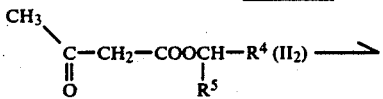

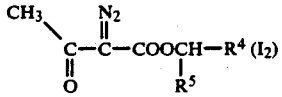

Process 3

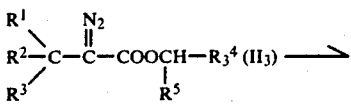

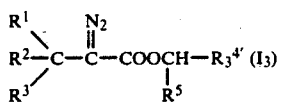

in which $R^1$, $R^2$, $R^3$, $R^4$ and $R^5$ are the same as defined above, $R_3^4$ is protected amino(lower)alkyl or protected amino-carboxy(lower)alkyl, and
$R_3^{4'}$ is amino(lower)alkyl or aminocarboxy(lower)alkyl.

In the above and subsequent description of the present specification, suitable examples and illustrations for the various definitions to be included within the scope of the invention are explained in detail as follows.

The term "lower" is intended to mean 1 to 6 carbon atom(s) unless otherwise indicated.

A suitable "lower alkyl" or lower alkyl moiety of "halo(lower)alkyl", "carboxy(lower)alkyl", "aminocarboxy(lower)alkyl", "protected amino(lower)alkyl" or "protected amino-carboxy(lower)alkyl" may include straight or branched ones such as methyl, ethyl, propyl, isopropyl, butyl, pentyl, hexyl and the like.

A suitable "halogen" in the term of "halo(lower)alkyl" may include fluorine and the like.

A suitable aryl may be phenyl, naphthyl, tolyl and the like.

A suitable "protected hydroxy" may include tetrahydropyranyloxy (e.g. 2-tetrahydropyranyloxy, etc.), acyloxy such as lower alkanoyloxy (e.g. acetoxy, propionyloxy, etc.) and the like, ar(lower)alkoxy such as mono(or di or tri)phenyl(lower)alkoxy (e.g. benzyloxy, trityloxy, etc.) and the like, lower alkoxy (e.g. methoxy, ethoxy, propoxy, etc.) and the like, and the like.

A suitable "protected amino" in the term of "protected amino(lower)alkyl" or "protected amino-carboxy(lower)alkyl" may include amino protected by a conventional amino-protective group which is used in the field of amino acid and peptide chemistry, and suitable "amino-protective group" may include acyl such as lower alkanoyl (e.g. formyl, acetyl, propionyl, etc.), halo(lower)alkanoyl (e.g. trifluoroacetyl, etc.), aroyl (e.g. benzoyl, etc.), lower alkoxycarbonyl (e.g. methoxycarbonyl, ethoxycarbonyl, propoxycarbonyl, etc.), ar(lower)alkoxycarbonyl [e.g. mono(or di or tri)phenyl(lower)alkoxycarbonyl (e.g. benzyloxycarbonyl, trytyloxycarbonyl, etc.), etc.] and the like.

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, dibenzylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, chloroacetate, trichloroacetate, maleate, tartrate, methanesulfonate, benzenesulfonate, p-toluenesulfonate, etc.); a salt with a basic or acidic amino acid (e.g. arginine salt, aspartate, glutamate, etc.); and the like.

The processes for preparing the object compounds (I) of the present invention are explained in detail in the following.

Process 1

A compound (I) or its salt can be prepared by reacting a compound (II₁) or its salt with alkali metal nitrite (e.g. potassium nitrite, sodium nitrite, etc.).

Suitable salts of the compound (II₁) may be the ones as exemplified for the compound (I).

The reaction can usually be carried out in a conventional solvent such as water and the like under cooling to warming.

Process 2

A compound ($I_2$) or its salt can be prepared by reacting a compound ($II_2$) or its salt with an azidating agent such as p-toluenesulfonyl azide.

Suitable salts of the compounds ($I_2$) and ($II_2$) may be ones as exemplified for the compound (I).

The reaction can usually be carried out in a conventional solvent such as alcohol (e.g. methanol, ethanol, etc.), water and the like under cooling to warming.

Process 3

A compound ($I_3$) or its salt can be prepared by subjecting a compound ($II_3$) or its salt to elimination reaction of the amino-protective group in $R_3^4$.

Suitable salts of the compound ($I_3$) and ($II_3$) may be the ones as exemplified for the compound (I).

This reaction can be carried out using a conventional chemical method such as hydrolysis, reduction and a conventional biological one, preferably by using acylase.

These reactions can usually be carried out in a conventional solvent such as alcohol (e.g. methanol, ethanol, etc.), water and the like under cooling to warming.

Some starting compounds are novel and such novel starting compounds can be prepared by a similar manner to the methods described in Preparations 1 to 32.

Among the amino acid derivatives (I), O-[2-diazo3(R)-hydroxy-1-oxobutyl]-L-serine (hereinafter referred to as FR-900840 substance) can also be produced by fermentation of FR-900840 substance-producing strain belonging to the genus Streptomyces such as Streptomyces sp. No. 8727 or the like in a nutrient medium.

The fermentation process is explained in detail in the following.

(i) Microorganism:

Particulars of the microorganism used for producing FR-900840 substance is explained in the following.

(a) Taxonomic studies on strain No. 8727:

Strain No. 8727 was isolated from a soil sample obtained from Ishioka-shi, IBARAKI Japan.

The methods described by Shirling and Gottlieb[*1] were employed for this taxonomic study. Morphological observations were made with light and electron microscopes from cultures grown at 30° C. for 21 days on yeast-malt extract agar, inorganic salts-starch agar and oatmeal agar and glucose-asparagine agar. Branching type of sporophores was monopodial and the form of mature sporophores was Spira with 20 to 70 spores in each chain. The spores were determined by electron microscopy to be oval and measured 0.6–0.7×0.9–1.1 μm in size. Spore surfaces were spiny. Neither fragmentation of hyphae nor formation of spores occurred in the substrate mycelium. Sporangia, sclerotia and zoospores were not observed.

Cultural characteristics were observed on ten media described by Shirling and Gottlieb[*1] and Waksman[*2]. Incubation was carried out at 30° C. for 21 days. The color names used in this study were taken from Methuen Handbook of Colour.[*3]. The aerial mass color belonged to blue color series when grown on yeast-malt extract agar and inorganic salts-starch agar. Soluble pigment was not produced. Results are shown in Table 1.

TABLE 1

Cultural characteristics of stain No. 8727

| Medium | Cultural characteristics | |
|---|---|---|
| yeast-malt extract agar | growth: | good |
| | aerial mass color: | bluish gray |
| | reverse side color: | yellowish brown |
| | soluble pigment: | none |
| oatmeal agar | growth: | moderate |
| | aerial mass color: | bluish gray |
| | reverse side color: | yellowish white |
| | soluble pigment: | none |
| inorganic salts-starch agar | growth: | good |
| | aerial mass color: | bluish gray |
| | reverse side color: | brown |
| | soluble pigment: | none |
| glycerin-asparagine agar | growth: | good |
| | aerial mass color: | none |
| | reverse side color: | yellowish brown |
| | soluble pigment: | none |
| peptone-yeast extract-iron agar | growth: | moderate |
| | aerial mass color: | none |
| | reverse side color: | grayish yellow |
| | soluble pigment: | none |
| tyrosine agar | growth: | good |
| | aerial mass color: | orange white |
| | reverse side color: | dark brown |
| | soluble pigment: | none |
| glucose-asparagine agar | growth: | good |
| | aerial mass color: | yellowish white |
| | reverse side color: | yellowish white |
| | soluble pigment: | none |
| nutrient agar | growth: | moderate |
| | aerial mass color: | none |
| | reverse side color: | yellowish white |
| | soluble pigment: | none |
| Bennet agar | growth: | good |
| | aerial mass color: | none |
| | reverse side color: | yellowish brown |
| | soluble pigment: | none |
| sucrose-nitrate agar | growth: | good |
| | aerial mass color: | none |
| | reverse side color: | yellowish brown |
| | soluble pigment: | none |

Cell wall analysis was performed by the methods of Becker et al.[*4] and Yamaguchi[*5]. Analysis of whole cell hydrolysates showed the presence of LL-diaminopimeric acid. Accordingly, the cell wall of this strain is classified as type I.

Physiological properties of strain No. 8727 were as follows.

Temperature range for growth was determined on yeast-malt extract agar using a temperature gradient incubator (Toyo Kagaku Sangyo Co., Ltd.). Summarized physiological properties of strain No. 8727 are shown in Table 2. Temperature range for growth was from 13° C. to 37° C. with optimum temperature from 30° C. to 32° C. Milk peptonization and gelatin liquefaction were positive. Production of melanoid pigment was positive on tyrosine agar.

TABLE 2

Physiological properties of stain No. 8727

| Conditions | Characteristics |
|---|---|
| temperature range for growth | 13° C.–37° C. |
| optimum temperature for growth | 30° C.–32° C. |
| starch hydrolysis | positive |
| milk coagulation | negative |
| milk peptonization | positive |
| production of melanoid pigment | positive |
| gelatin liquefaction | positive |
| decomposition of cellulose | negative |

Utilization of carbon sources was examined according to the method of Pridham and Gottlieb[*6]. The results were determined after 14 days incubation at 30° C. This strain could utilize all carbon sources tested for growth as shown in the following Table 3.

TABLE 3

| Carbon utilization of strain No. 8727 | |
|---|---|
| Compounds | Growth |
| D-glucose | + |
| sucrose | + |
| D-xylose | + |
| D-fructose | + |
| L-ramnose | + |
| raffinose | + |
| L-arabinose | + |
| inositol | + |
| mannitol | + |

+: utilization

Referring to Bergey's Manual[*7] or ISP report[*8] [*9] [*10] about the results of taxonomic studies presented here, the inventors conclude that strain No. 8727 belongs to the genus Streptomyces Waksman and Henrici 1943. Then, the inventors identified this strain as one strain of Streptomyces and named it Streptomyces sp. No. 8727.

(*1) Shirling, E. B. and D. Gottlieb: Methods for characterization of Streptomvces species: Intern. J. Syst. Bacteriol. 16 : 313-340, 1966

(*2) Waksman, S. A.: The actinomycetes Vol. 2 Classification, identification and description of genera and species: The Williams and Wilkins Co., Baltimore, 1961

(*3) Kornerup, A. and J. H. Wanscher: Methuen Handbook of Colour: Methuen, London, 1978

(*4) Becker, B., M. P. Lechevalier, R. E. Gordon and H. A. Lechevalier: Rapid differentiation between Nocardia and Streptomyces by paper chromatography of whole-cell hydrolysates: Appl. Microbiol. 12, 421-423, 1964

(*5) Yamaguchi, T.: Comparison of the cell-wall composition of morphologically distinct actinomycetes: J. Bacteriol. 89, 444-453, 1965

(*6) Pridham, T. G. and D. Gottlieb: The utilization of carbon compounds by some Actinomycetales as an aid for species determination: J. Bacteriol. 56: 107-114, 1948

(*7) Buchanan, R. E. and N. E. Gibbons : Bergey's manual of determinative bacteriology, eight edition: The Williams and Wilkins Co., Baltimore, 1974

(*8) Shirling, E. B. and D. Gottlieb: Cooperative description of type culture of Streptomyces: 2. Species descriptions from first study: Intern. J. Syst. Bacteriol. 18: 69-189, 1968

(*9) Shirling, E. B. and D. Gottlieb: Cooperative description of type culture of Streptomyces: 3. Additional species descriptions from first and second studies: Intern. J. Syst. Bacteriol. 18: 279-392, 1968

(*10) Shirling, E B. and D. Gottlieb: Cooperative description of type culture of Streptomyces: 4. Species descriptions from the second, third and forth studies: Intern. J. Syst. Bacteriol. 19: 391-512, 1969

A culture of Streptomyces sp. No. 8727 has been deposited with Fermentation Research Institute Agency of Industrial Science and Technology (1-3, Higashi 1 chome, Tsukuba-shi, IBARAKI 305 JAPAN) on March 19, 1987 under the number of FERM P-9296, and then said culture was transferred to Budapest Treaty route of the same depository on March 18, 1988 under the new deposit number of FERM BP-1804.

(ii) Production of FR-900840 substance

FR-900840 substance of this invention is produced when a FR-900840 substance-producing stain belonging to the genus Streptomyces (e.g. Streptomyces sp. No. 8727) is grown in a nutrient medium containing sources of assimilable carbon and nitrogen under aerobic conditions (e.g. shaking culture, submerged culture, etc.).

The preferred sources of carbon in the nutrient medium are carbohydrates such as xylose, glucose, sucrose, fructose, starch and the like.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea, amino acid and the like.

The carbon and nitrogen sources, though advantageously employed in contination, need not to be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, cobalt salts and the like.

If necessary, especially when the culture medium foams seriously, a defoaming agent, such as liquid paraffin, fatty oil, plant oil, mineral oil or silicone may be added.

As in the case of the preferred methods used for the production of other biologically active substances in massive amounts, submerged aerobic cultural conditions are preferred for the production of FR-900840 substance in massive amounts.

For the production in small amounts, a shaking or surface culture in a flask or bottle is employed.

Further, when the growth is carried out in large tanks, it is preferable to use the vegetative form of the organism for inoculation in the production tanks in order to avoid growth lag in the process of production of FR-900840 substance. Accordingly, it is desirable first to produce a vegetative inoculum of the organism by inoculating a relatively small quantity of culture medium with spores or myceria of the organism and culturing said inoculated medium, and then to transfer the cultured vegetative inoculum to large tanks. The medium, in which the vegetative inoculum is produced, is substantially the same as or different from the medium utilized for the production of FR-900840 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 15° C. and 35° C., preferably 20° C. to 30° C., for a period of about 50 hours to 100 hours, which may be varied according to fermentation conditions and scales.

When the fermentation is completed, the culture broth is then subjected for recovery of FR-900840 substance to various procedures conventionally used for recovery and purification of biological active substances, for instance, solvent extraction with an appropriate solvent or a mixture of some solvents, chromatography or recrystallization from an appropriate solvent or a mixture of some solvents.

According to this invention, in general, FR-900840 substance is found mainly out of the cultured mycelia. Accordingly, the culture broth is separated by means of filtration or centrifuging to remove the mycelia, and then FR-900840 substance is removed from the filtrate by means of extraction using an appropriate organic solvent such as acetone, ethyl acetate or the like, or a mixture of these solvents.

The extract is treated by a conventional manner to provide FR-900840 substance, for example, the extract is concentrated by evaporation or distillation to a smaller amount and the resulting residue containing active material, i.e. FR-900840 substance is purified by conventional purification procedures, for example, chromatography or recrystallization from an appropriate solvent or a mixture of some solvents. (iii) Physicochemical properties of FR-900840 substance FR-900840 substance as obtained according to the aforementioned fermentation process has the following physical and chemical properties.

Form and color: pale yellowish prism
Molecular formula: $C_7H_{11}N_3O_5$
Molecular weight: 217 [FAB-MS 218 (M+H)+]
Elemental Analysis: Found: C, 35.99; H, 5.58; N, 17.65 (%) Calcd: for $C_7H_{11}N_3O_5 \cdot H_2O$ C, 35.74; H, 5.57; N, 17.87 (%)

Color reaction: positive: cerium sulfate reaction, sulfuric acid reaction, ninhydrin reaction, ferric chloride reaction, iodine vapor reaction negative: Ehrlich reaction, Dragendorff reaction, Molish reaction Solubility: soluble: water sparingly soluble: methanol, ethanol insoluble: acetone, chloroform, ethyl acetate, diethyl ether, benzene Melting point: 123°–125° C. (dec)
Specific rotation: $[\alpha]_D^{23}$: +1.5° (c=1.0, $H_2O$)
Ultraviolet absorption spectrum: $\lambda_{max}^{H_2O}=257.5$ nm (e=13,000) $\lambda_{max}^{H_2O+HCl}=257.0$ nm $\lambda_{max}^{H_2O+NaOH}=257.0$ nm Thin layer chromatography: Rf value (silica plate): 0.24 (chloroform:methanol:aqueous $NH_4OH=5:3:1$), 0.44 (n-buthanol:ethanol:chloroform:aqueous $NH_4OH=2:2:1:2$)

Infrared absorption spectrum: $\lambda_{max}^{Nujol}=3430$, 3270, 3100, 2920, 2260, 2100, 1660, 1610, 1560, 1525, 1460, 1410, 1380, 1350, 1295, 1235, 1160, 1140, 1090, 1070, 1010, 965, 900, 845, 820, 790, 740, 705 cm$^{-1}$ $^1H$ Nuclear magnetic resonance spectrum: (200.13 MHz, $D_2O$ used dioxane as internal standard) δ: 4.87 (1H, q, J=6.6Hz), 4.62 (2H, d, J=3.8Hz), 4.10 (1H, t, J=3.8Hz), 1.42 (3H, d, J=6.6Hz)

$^{13}C$ Nuclear magnetic resonance spectrum: (50.23 MHz, $D_2O$ used dioxane as internal standard) δ: 173.55(s), 169.99(s), 66.15(t), 64.74(d), 56,67(d), 22.15(q)

Amino acid derivatives (I) can be transferred to its suitable pharmaceutically acceptable salts by a conventional manner.

Biological properties of amino acid derivatives (I)
As examples for showing pharmacological activities of the amino acid derivatives (I), pharmacological data of some compounds of the amino acid derivatives (I) are explained in the following.

Test 1
Inhibition of human lung adenocarcinoma A549 cell growth in vitro by some compounds of the amino acid derivatives (I)

The cytotoxicity test was performed in microtiter plates, with each well containing $3 \times 10^3$ A549 cells in 100 μl Dulbecco's minimum essential medium supplemented with 10% fetal calf serum, penicillin (50 units/ml) and streptomycin (50 μg/ml). The cells were incubated at 37° C. for seven days and the colorimetric MTT (tetrazolium) assay was performed according to the method described by Mosmann (J. Immunol. Methods, 65, 55–63, 1983). MTT [3-(4,5-dimethylthiazol-2-yl)-2,5-diphenyl tetrazolium bromide, made by Sigma] was dissolved in PBS at 5 mg/ml and filtered to sterilize and remove a small amount of insoluble residue. After the culture of A549 cells was terminated, this MTT solution (10 μl per 100μl medium) was added to plates were further incubated at 37° C. for 4 hours. Acid-isopropanol (100 μl of 0.04N HCl in isopropanol) was added to all wells and mixed thoroughly to dissolve the dark blue crystals. After all crystals were dissolved, the plates were read on a 2-wavelength microplate photometer (Model MTP-22; Corona Electric Co., Ltd., Katsuta, Japan) at 550 nm, a reference wavelength of 660 nm. The object compound of this invention was dissolved and diluted in Dulbecco's minimum essential medium and added to the culture to give final concentration of 30μg/ml or less. The result is shown in Table 4.

TABLE 4

| Effect of some compounds of the amino acid derivatives (I) on human adenocarcinoma A549 cell growth | |
|---|---|
| Compounds | $IC_{50}$ (μg/ml) |
| a compound of Example 1 | $1.2 \times 10^{-5}$ |
| a compound of Example 2 | $1.05 \times 10^{-5}$ |
| a compound of Example 4 | $1.8 \times 10^{-5}$ |
| a compound of Example 5 | $1.4 \times 10^{-4}$ |
| a compound of Example 6 | $1.8 \times 10^{-6}$ |

Test 2
Inhibition of human mammary adenocarcinoma MCF-7 cell growth in vitro by some compounds of the amino acid derivatives (I)

The cytotoxicity test was performed in microtiter plates, with each well containing $3 \times 10^3$ MCF-7 cells in 100 μl Eagle's minimum essential medium supplemented with 10% fetal calf serum, sodium pyruvate, nonessential amino acids, penicillin (50 units/ml) and streptomycin (50 μg/ml). The cells were incubated at 37° C. for seven days in humidified atomosphere of 5% carbon dioxide and 95% of air and the colorimetric MTT assay was performed as described in Test 1.

The test compound was dissolved and diluted in Eagle's minimum essential medium and added to the culture to give final concentration of 30 μg/ml or less. The result is shown in Table 5.

TABLE 5

| Effect of some compounds of the amino acid derivatives (I) on human mammary adenocarcinoma MCF-7 cell growth | |
|---|---|
| Compounds | $IC_{50}$ (μg/ml) |
| a compound of Example 1 | $1.8 \times 10^{-6}$ |
| a compound of Example 2 | $6.8 \times 10^{-6}$ |
| a compound of Example 4 | $8.2 \times 10^{-7}$ |
| a compound of Example 5 | $7.6 \times 10^{-5}$ |
| a compound of Example 6 | $1.7 \times 10^{-6}$ |

Test 3
Acute toxicity of FR-900840 substance

Acute toxicity of FR-900840 substance in BDF$_1$ mice by intravenous injection is 180 mg/kg.

From the test results, it is realized that amino acid derivatives (I) have an anti-tumor activity.

The pharmaceutical composition of this invention can be used in the form of a pharmaceutical preparation, for example, in solid, semisolid or liquid form, which contains an amino acid derivative (I) or its pharmaceutically acceptable salt, as an active ingredient in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. And, if necessary, in addition, auxiliary, stabilizing, thickening and coloring agents and perfumes may be used. An amino acid derivative (I) or its pharmaceutically acceptable salt may be included in the pharmaceutical composition in an amount sufficient to produce the desired antitumor effect upon the process or condition of diseases.

For applying the composition to human, it is preferable to apply it by intravenous, intramuscular or oral administration. While the dosage of therapeutically effective amount of an amino acid derivative (I) or its pharmaceutically acceptable salt varies from and also depends upon the age and condition of each individual patient to be treated, in the case of intravenous administration, a daily dose of 0.1–100 mg of an amino acid derivative or its pharmaceutically acceptable salt per kg weight of human being, in the case of intramuscular administration, a daily dose of 0.1–100 mg of an amino acid derivative (I) or its pharmaceutically acceptable salt per kg weight of human being, in case of oral administration, a daily dose of 0.1–100 mg of an amino acid derivative or its pharmaceutically acceptable salt per kg weight of human being is generally given for treating tumor.

The following examples are given for the purpose of illustrating the present invention in more detail.

PREPARATION 1

Benzyl O-(N-benzyloxycarbonyl-O-benzyl-L-threonyl)-N-(trifluoroacetyl)-L-serinate To a solution of N-benzyloxycarbonyl-O-benzyl-L-threonine (3.4 g, 10 mmol) in anhydrous ethyl acetate (10 ml) containing N-methylmorpholine (1.09 ml, 10 mmol) was added at -15° C. a solution of pivaloyl chloride (1.22 ml, 10 mmol) in anhydrous ethyl acetate (5 ml) over 5 minutes with stirring. The mixture was further stirred for 30 minutes at the same temperature and then cooled to −78° C. A solution of N-(trifluoroacetyl)-L-serine benzyl ester (2.9 g, 10 mmol) and 4-N,N-dimethylaminopyridine (0.12 g, 1 mmol) in anhydrous ethyl acetate (10 ml) was added over a 5 minutes with stirring. After complete addition, the cooling bath was removed and the mixture was stirred at room temperature overnight. The reaction mixture was washed successively with 2N hydrochloric acid, water, 10% aqueous sodium hydrogen carbonate, water and brine and dried over magnesium sulfate. Removal of the solvent gave an oil (6 g) which was purified by silica gel column (CHCl$_3$) to afford 4.0 g of pure benzyl O-(N-benzyloxycarbonyl-O-benzyl-L-threonyl)-N-(trifluoroacetyl)-L-serinate as an oil.

IR(CHCl$_3$) 3400, 3000, 1740, 1720, 1500, 1170 cm$^{-1}$

NMR (CDCl$_3$) δ 7.65 (1H, d, J=8Hz), 7.40–7.20 (15H, m), 5.43 (1H, d, J=8Hz), 5.20 (2H, s), 5.17 (1H, d, J=12Hz), 5.08 (1H, d, J=12Hz), 4.88 (1H, dt, J=8, 3Hz), 4.68 (1H, dd, J=11.5, 3Hz), 4.50 (1H, d, J=11.5Hz), 4.47 (1H, dd, J=11.5, 3Hz), 4.36 (1H, d, J=11.5Hz), 4.24 (1H, dd, J=8, 3Hz), 4.03 (1H, dq, J=3, 7Hz), 1.20 (3H, d, J=7Hz) ;

FAB-MS m/z 617 (M+H) [α]$_D^{23}$ −15° (c=1.0, methanol)

PREPARATION 2

O-(L-Threonyl)-N-(trifluoroacetyl)-L-serine

Benzyl O-(N-benzyloxycarbonyl-O-benzyl-L-threonyl)-N-(trifluoroacetyl)-L-serinate (500 mg) was dissolved in acetic acid (10 ml) and the solution was hydrogenated over 10% palladium on activated carbon at 40 psi (500 mg) under 3 atomospheric pressure of hydrogen at room temperature for 1 hour. The mixture was filtered and the filtrate was evaporated to dryness. The residue was dissolved in a small amount of methanol and the solution was diluted with diethyl ether to give a white precipitate. The precipitate was crystallized from aqueous methanol to give 230 mg of pure O-(L-threonyl)-N-(trifluoroacetyl)-L-serine as a white powder.

IR (Nujol) 3600–2400, 1740, 1700, 1450, 1400 cm$^{-1}$

NMR (D$_2$) δ 4.72 (1H, dd, J=13, 5Hz), 4.52–4.48 (2H, m), 4.23 (1H, dq, J=4, 7Hz), 3.77 (1H, d, J=4Hz), 1.26 (3H, d, J=7Hz)

FAB-MS m/z 303 (M+H)

[α]$_D^{23}$ +7° (c=1.0, H$_2$O)

PREPARATION 3

Benzyl O-(O-benzyl-N-benzyloxycarbonyl-R-threonyl)-N-trifluoroacetyl-L-serinate To a solution of O-benzyl-N-benzyloxycarbonyl-R-threonine (1 g), benzyl N-trifluoroacetyl-L-serinate (844 mg), and 4-N,N-dimethylaminopyridine (35.4 mg) in methylene chloride (20 ml) was added N,N-diethylaminopropyl-N′-ethylcarbodiimide hydrochloride (554 mg) at 0° C. The reaction mixture was allowed to warm to room temperature and stirred at room temperature for an hour. The reaction mixture was diluted with ethyl acetate and washed successively with 0.1 N hydrochloric acid, water, 10% aqueous sodium hydrogen carbonate, water and brine. After drying over sodium sulfate, the ethyl acetate extract was filtered and concentrated. The residue was chromatographed on silica gel eluting successively with a 1:1 mixture of methylene chloride and hexane, methylene chloride and a 50:1 mixture of methylene chloride and acetone to give benzyl O-(O-benzyl-N-benzyloxycarbonyl-R-threonyl)-N-trifluoroacetyl-L-serinate (1.71 g).

NMR (CDCl$_3$) δ 1.25 (3H, d, J=6Hz), 3.9 to 4.1 (1H, m), 4.2 to 4.4 (2H, m), 4.4 to 4.7 (3H, m), 4.7 to 4.9 (1H, m), 5.0 to 5.3 (4H, m), 5.52(1H, d, J=9Hz), 7.1 to 7.5 (16H, m)

PREPARATION 4

O-(R-Threonyl)-N-trifluoroacetyl-L-serine

A mixture of benzyl O-(O-benzyl-N-benzyloxycarbonyl-R-threonyl)-N-trifluoroacetyl-L-serinate (1 g) and 10% palladium on activated carbon (1 g) in acetic acid (30 ml) was hydrogenated at 40 psi under hydrogen at room temperature for 6 hours. The reaction mixture was filtered with Celite (filter aid, trade mark, made by Nakarai Chemicals) and evaporated. The residue was diluted with water and lyophylized to give O-(R-threonyl-N-trifluoroacetyl-L-serine (425 mg).

NMR (D$_2$O) δ 1.35(3H, d, J=6Hz), 4.11 (1H, d, J=4Hz),
4.30 to 4.45 (1H, m), 4.50 to 4.75 (3H, m)

PREPARATION 5

Benzyl O-(N-benzyloxycarbonyl-3-phenyl-O-tetrahydropyranyl-D,L-serinyl)-N-trifluoroacetyl-L-serinate To a solution of N-benzyloxycarbonyl-3-phenyl-O-tetrahydropyranyl-D,L-serine (1 g) and N-methylmorpholine (252 mg) in ethyl acetate (10 ml) was added pivaloyl chloride (308 μl) at −15° C. After stirring for 20 minutes at −15° C., the reaction mixture was cooled to −78° C. To the reaction mixture was added benzyl N-trifluoroacetylserinate (840 mg) and 4-N,N-dimethylaminopyridine (31 mg) at −78° C. The mixture was allowed to warm to room temperature and stirred for an hour at room temperature. The reaction mixture was diluted with ethyl acetate and washed successively with 2N hydrochloric acid, water, 10% aqueous sodium hydrogen carbonate, water and brine. After drying over magnesium sulfate, the ethyl acetate extract was filtered and concentrated to give benzyl -(N-benzyloxycarbonyl-3-phenyl-tetrahydropyranyl)-D,L-serinyl)-N-trifluoroacetyl-L-serinate (1.6 g).

PREPARATION 6

Benzyl O-(N-benzyloxycarbonyl-3-phenyl-D,L-serinyl)-N-trifluoroacetyl-L-serinate To a solution of benzyl O-(N-benzyloxycarbonyl-3-phenyl-O-tetrahydropyranyl-D,L-serinyl)-N-trifluoroacetyl-L-serinate (0.8 g) in methanol (10 ml) was added p-toluenesulfonic acid (45.6 mg) at room temperature. After stirring for an hour at room temperature, the reaction mixture was concentrated and the residue was chromatographed on preparative thin layer chromatography to give benzyl O-(N-benzyloxycarbonyl-3-phenyl-D,L-serinyl)-N-trifluoroacetyl-L-serinate (404 mg).

NMR (CDCl$_3$) δ 4.4 to 4.7 (3H, m), 4.8 to 5.3 (5H, m), 5.4 to 5.7 (1H, m), 7.1 to 7.5 (15H, m), 7.6 to 7.8 (1H, m)

PREPARATION 7

O-(3-Phenyl-D,L-serinyl)-N-trifluoroacetyl-L-serine

A mixture of benzyl O-(N-benzyloxycarbonyl-3-phenyl-D,L-serinyl)-N-trifluoroacetyl-L-serinate (324 mg) and 10% palladium on activated carbon (400 mg) in acetic acid (5 ml) was hydrogenated at 40 psi under hydrogen at room temperature for 2 hours. The reaction mixture was filtered with Celite (filter aid, trade mark, made by Nakarai Chemicals) and concentrated and lyophilized to give O-(3-phenyl-D,L-serinyl)-N-trifluoroacetyl-L-serine (150 mg).

NMR (D$_2$O) δ 4.25 to 4.35 (1H, m), 4.5 to 4.7 (3H, m), 5.3 to 5.4 (1H, m), 7.3 to 7.6 (5H, m)

PREPARATION 8

Benzyl O-(O-benzyl-N-benzyloxycarbonyl-L-serinyl)-N-trifluoroacetyl-L-serinate

To a solution of O-benzyl-N-benzyloxycarbonyl-L-serine (1 g) and benzyl N-trifluoroacetyl-L-serinate (873 mg) in methylene chloride (20 ml) was added N,N-diethylaminopropyl-N'-ethylcarbodiimide hydrochloride (573 mg) and -N,N-dimethylaminopyridine (37 mg) at 0° C. The reaction mixture was allowed to warm to room temperature and stirred for an hour at room temperature. The reaction mixture was diluted with ethyl acetate (200 ml) and washed successively with 0.2N hydrochloric acid, water, 10% aqueous sodium hydrogen carbonate, water and brine. After drying over sodium sulfate, the ethyl acetate extract was filtered and concentrated. The residue was chromatographed on silica gel eluting successively with a 1:1 mixture of methylene chloride and hexane, methylene chloride, a 50:1 mixture of methylene chloride and acetone to give benzyl O-(O-benzyl-N-benzyloxycarbonyl-L-serinyl)-N-trifluoroacetyl-L,-serinate (1.5 g).

NMR (CDCl$_3$) δ 3.55 to 3.8 (2H, m), 4.2 to 4.6 (4H, m), 4.3 to 5.3 (6H, m), 5.5 (1H, m), 7.1 to 7.5 (15H, m), 7.55 to 7.8 (1H, m)

PREPARATION 9

O-(L-Serinyl)-N-trifluoroacetyl-L-serine

A mixture of benzyl O-(O-benzyl-N-benzyloxycarbonyl-L-serinyl)-N-trifluoroacetyl-L-serinate (1 g) and 10% palladium on activated carbon (1 g) in acetic acid (30 ml) was hydrogenated under hydrogen at 40 psi at room temperature for 6 hours. The reaction mixture was filtered with Celite (filter aid, trade mark, made by Nakarai Chemicals) and the filtrate was concentrated in vacuo and the residue was diluted with water (50 ml) and lyophylized to give O-(L-serinyl)-N-trifluoroacetyl-L-serine (430 ml).

NMR (D$_2$O) δ 3.9 to 4.2 (2H, m), 4.3 (1H, t, J=4Hz), 4.5 to 4.8 (3H, m)

PREPARATION 10

Benzyl O-acetoacetyl-N-trifluoroacetyl-L-serinate

A solution of benzyl trifluoroacetyl-L-serinate (500 mg) and diketene (0.1 ml) in tetrahydrofuran (10 ml) was heated with reflux overnight. The solvent was distilled off and the residue was diluted with ethyl acetate and washed successively with water and brine. After drying over sodium sulfate, the ethyl acetate extract was filtered and concentrated. The residue was chromatographed on silica gel eluting successively with methylene chloride and a 4:1 mixture of methylene chloride and acetone to give benzyl O-acetoacetyl-N-trifluoroacetyl-L-serinate (320 mg).

PREPARATION 11

O-Acetoacetyl-N-trifluoroacetyl-L-serine

A mixture of benzyl O-acetoacetyl-N-trifluoroacetyl-L-serinate (320 mg) and 10% palladium on activated carbon (40 mg) in ethanol (10 ml) was hydrogenated under hydrogen at one atom for 20 minutes. The mixture was filtered with Celite (filter aid, trade mark, made by Nakarai Chemicals) and the filtrate was concentrated to give O-acetoacetyl-N-trifloroacetyl-L-serine (232 mg).

NMR (CDCl$_3$) δ 2.30(3H, s), 3.6 (2H, s), 4.55 (1H, dd, J=2 and 6Hz), 4.82 (1H, dd, J=2 and 4Hz), 4.94 (1H, dd, J=4 and 6Hz), 7.82 (1H, broad d, J=4Hz)

PREPARATION 12

2-Benzyloxycarbonylethyl O-benzyl-N-benzyloxycarbonyl-L-threonate

To a solution of O-benzyl-N-benzyloxycarbonyl-L-threonine (1.15 g), benzyl 3-hydroxypropionate (604 mg) and 4-N,N-dimethylaminopyridine (41 mg) in methylene chloride (20 ml) was added N,N-diethylaminopropyl-N'-ethylcarbodiimide hydrochloride (641 mg) at 0° C. The reaction mixture was allowed to warm to room temperature and stirred at room temperature for an hour. The reaction mixture was concentrated and the residue was diluted with ethyl acetate and washed successively with 0.1 N hydrochloric acid, water, 10% aqueous sodium hydrogen carbonate, water and brine. After drying over sodium sulfate, the ethyl acetate extract was filtered and concentrated. The residue was chromatographed on silica gel eluting successively with a 1:1 mixture of methylene chloride and hexane, methyl chloride and a 50:1 mixture of methylene chloride and acetone to give 2-benzyloxycarbonylethyl O-benzyl-N-benzyloxycarbonyl-L-threonine (1.1 g).

NMR (CDCl$_3$) δ 1.25 (3H, d, J=7Hz), 2.60 (2H, t, J=7.5Hz), 4.07 (1H, dq, J=2.5 and 7Hz), 4.20 to 4.55 (5H, m), 5.11 (2H, s), 5.12 (2H, s), 5.5 (1H, d, J=10Hz), 7.1 to 7.4 (15H, m)

PREPARATION 13

2-Carboxyethyl L-threonate

A mixture of 2-benzyloxycarbonylethyl O-benzyl-N-benzyloxycarbonyl-L-threonate (1.1 g) and 10% palladium on activated carbon (700 mg) in acetic acid (30 ml) was hydrogenated at 40 psi under hydrogen at room temperature for 5 hours. The reaction mixture was filtered with Celite (filter aid, trade mark, made by Nakarai Chemicals) and concentrated. The residue was diluted with water and lyophylized to give 2-carboxyethyl L-threonate (400 mg).

NMR (D$_2$O) δ 1.35 (3H, d, J=7Hz), 2.61 (2H, t, J=6.5Hz), 4.19 (1H, d, J=4.4Hz), 4.3 to 4.6 (3H, m)

PREPARATION 14

N-(2-Hydroxyethyl)trifluoroacetamide

To a solution of methyl trifluroracetate (6.67 ml) and triethylamine (5.54 ml) in methanol (70 ml) was added 2-aminoethanol (2 ml) at room temperature. After stirring for an hour at room temperature, the reaction mixture was concentrated and the residue was diluted with ethyl acetate (200 ml) and washed successively with aqueous hydrogen chloride, water, 10% aqueous sodium hydrogen carbonate and brine. After drying over sodium sulfate, the ethyl acetate extract was filtered and concentrated to give N-(2-hydroxyethyl)trifluoroacetamide (3.84 g).

NMR (CDCl$_3$) δ 3.52 (2H, dt, J=3 and 4Hz), 3.80 (2H, t, J=4Hz), 7.00 (1H, broad s)

PREPARATION 15

2-Trifluoroacetamidoethyl O-benzyl-N-benzyloxycarbonyl-L-threonate

To a solution of O-benzyl-N-benzyloxycarbonyl-L-threonine (2.2 g) and N-(2-hydroxyethyl)trifluoroacetamide (1 g) in methylene chloride (44 ml) was added N,N-diethylaminopropyl-N'-ethylcarbodiimide hydrochloride (1.22 g) and N,N-dimethylaminopyridine (77.8 mg) at room temperature. After stirring for an hour at room temperature, the reaction mixture was diluted with ethyl acetate (400 ml) and washed successively with aqueous hydrogen chloride, water, 10 % aqueous sodium hydrogen carbonate and brine. After drying over sodium sulfate, the ethyl acetate extract was filtered and concentrated. The residue was chromatographed on silica gel (60 g) eluting successively with a mixture of methylene chloride and hexane (1:1 to 3:1), methylene chloride and a mixture of methylene chloride and acetone (240:1) to give 2-trifluoroacetamidoethyl O-benzyl-N-benzyloxycarbonyl-L-threonate (2.54 g).

NMR (CDCl$_3$) δ 1.28 (3H, d, J=3Hz), 3.3 to 3.6 (2H, m), 4.05 to 4.22 (2H, m), 4.25 to 4.40 (2H, m), 4.50 (2H, ABq, J=6 and 22Hz), 5.12 (2H, s), 5.56 (1H, broad d), 7.2 to 7.4 (10H, m)

PREPARATION 16

2-Trifluoroacetamidoethyl L-threonine

A mixture of 2-trifluoroacetamidoethyl O-benzyl-N-benzyloxycarbonyl-L-threonate (100 mg) and 10% palladium on activated carbon (50 mg) in acetic acid (10 ml) was hydrogenated under hydrogen at 4 psi at room temperature for 3 hours. The mixture was filtrated with Celite (filter aid, trade mark, made by Nakarai Chemicals) and the filtrate was concentrated. The residue was chromatographed on preparative thin layer chromatography eluting with a mixture of chloroform, methanol and water (65:25:4) to give 2-trifluoroacetamidoethyl L-threonine (58 mg).

NMR (D$_2$O) δ 1.35 (3H, d, J=3Hz), 3.65 to 3.75 (2H, m), 4.12 (1H, d, J=2Hz), 4.35 to 4.50 (3H, m)

PREPARATION 17

Benzyl N-trifluoroacetyl-L-homoserinate

To a solution of L-homoserine (10 g) and triethylamine (11.7 ml) in methanol (50 ml) was added methyl trifluoroacetate (12.7 ml) at room temperature and the mixture was stirred overnight at room temperature The resulting mixture was evaporated and the residue was dissolved in N,N-dimethylformamide (50 ml) and triethylamine (11.7 ml) was added. To the mixture was added benzyl bromide (29.9 ml) at room temperature and the mixture was stirred overnight at room temperature The resulting mixture was evaporated and diluted with ethyl acetate and washed successively with 0.2N hydrochloric acid, water, 10% aqueous sodium hydrogen carbonate and brine. After drying over sodium sulfate, the ethyl acetate extract was filtered and concentrated to give benzyl N-trifluoroacetyl-L-homoserine (18.4 g).

NMR (CDCl$_3$) δ 2.1 to 2.4 (2H, m), 3.5 to 3.8 (2H, m), 4.7 to 4.9 (1H, m), 5.1 to 5.3 (2H, m), 7.1 to 7.5 (5H, m)

PREPARATION 18

Benzyl O-(O-benzyl-N-benzyloxycarbonyl-L-threonyl)-N-trifluoroacetyl-L-homoserinate To a solution of O-benzyl-N-benzyloxycarbonyl-L-threonine (1.5 g), benzyl N-trifluoroacetyl-L-homoserinate (1.34 g) and 4-N,N-dimethylaminopyridine (48.8 mg) in methylene chloride (30 ml) was added N,N-diethylaminopropyl-N'-ethylcarbodiimide hydrochloride (840 mg) at 0° C. After stirring for an hour at room temperature, the reaction mixture was concentrated. The residue was dissolved in ethyl acetate and washed successively with 0.1N hydrochloric acid, water, 10% aqueous sodium hydrogen carbonate, water and brine. After drying over sodium sulfate, the ethyl acetate extract was filtered and concentrated. The residue was chromatographed on silica gel eluting successively with a 1:1 mixture of methylene chloride and hexane, methylene chloride and a 50:1 mixture of methylene chloride and acetone (50:1) to give benzyl O-(O-benzyl-N-benzyloxycarbonyl-L-threonyl)-N-trifluoroacetyl-L-homoserinate (1.6 g).

NMR (CDCl₃) δ 1.25 (3H, d, J=7Hz), 2.0 to 2.3 (2H, m), 3.9 to 4.4 (5H, m), 4.5 to 4.7 (2H, m), 5.10 (2H, s), 5.17 (2H, s), 5.54 (1H, d, J=8Hz), 7.1 to 7.5 (15H, m)

PREPARATION 19

O-L-Threonyl-N-trifluoroacetyl-L-homoserine

A mixture of benzyl O-(O-benzyl-N-benzyloxycarbonyl-L-threonyl)-N-trifluoroacetyl-L-homoserinate (1.8 g) and 10% palladium on activated carbon (0.9 g) in acetic acid (30 ml) was hydrogenated in 40 psi under hydrogen at room temperature for 6 hours. The reaction mixture was filtered with Celite (filter aid, trade mark, made by Nakarai Chemicals) and the filtrate was concentrated. The residue was diluted with water and lyophilized to give 0-L-threonyl-N-trifluoroacetyl-L-homoserine (800 mg).

NMR (D₂O) δ 1.37 (3H, d, J=7Hz), 2.1 to 2.6 (2H, m), 4.13 (1H, d, J=3Hz), 4.3 to 4.6 (4H, m)

PREPARATION 20

O-Acetyl-N-benzyloxycarbonyl-L-threonine

To a solution of N-benzyloxycarbonyl-L-threonine (5 g) in acetic acid (50 ml) was added acetyl bromide (1.75 ml) at room temperature. After stirring for an hour at room temperature, the reaction mixture was concentrated and the residue was diluted with ethyl acetate and washed successively with water (2 times) and brine. After drying over sodium sulfate, the ethyl acetate extract was filtered and concentrated to give O-acetyl-N-benzyloxycarbonyl-L-threonine (3.64 g).

NMR (CDCl₃) δ 1.33 (3H, d, J=3Hz), 2.00 (3H, s), 5.15 (2H, s), 5.4 to 5.6 (2H, m), 7.3 to 7.5 (5H, m)

Mass (M+1) 296

PREPARATION 21

Benzyl O-[(3(R)-acetoxy-2(S)-benzyloxycarbonylamino-1-oxobutyl]-N-trifluoroacetyl-L-serinate To a solution of O-acetyl-N-benzyloxycarbonyl-L-threonine (1 g) and benzyl N-trifluoroacetyl-L-serinate (987 mg) in methylene chloride (20 ml) was added N,N-diethylaminopropyl-N'-ethylcarbodiimide hydrochloride (1.22 g) and 4-N,N-dimethylaminopyridine (77.8 mg) at room temperature. After stirring for an hour at room temperature, the reaction mixture was washed successively with aqueous hydrogen chloride, water, 10% aqueous sodium hydrogen carbonate and brine. After drying over sodium sulfate, the methylene chloride extract was filtered and concentrated. The residue was chromatographed on silica gel (20 g) eluting successively with a mixture of hexane and methylene chloride (1:1), methylene chloride and a mixture of methylene chloride and acetone (125:1) to give benzyl O-[3(R)-acetoxy-2(S)-benzyloxycarbonylamino-1-oxobutyl]-N-trifluoroacetyl-L-serinate (1.42 g).

NMR (CDCl₃) δ 1.25 (3H, d, J=3Hz), 2.00 (3H, s), 4.20 to 4.60 (4H, m), 5.10 to 5.40 (5H, m), 7.3 to 7.4 (10H, m), 7.95 (1H, broad s, J=3Hz)

Mass (M+1) 569

PREPARATION 22

O-[3(R)-Acetoxy-2(S)-amino-1-oxobutyl]-N-trifluoroacetyl-L-serine

A mixture of benzyl O-[3(R)-acetoxy-2(S)-benzyloxycarbonylamino-1-oxobutyl]-N-trifluoroacetyl-L-serinate (1.42 g) and 10% palladium on activated carbon (300 mg) in acetic acid (50 ml) was hydrogenated under hydrogen at 40 psi at room temperature for 2 hours. The mixture was filtered with Celite (filter aid, trade mark, made by Nakarai Chemicals) and the filtrate was concentrated. The residue was diluted with water and lyophilized to give O-[3(R)-acetoxy-2(S)-amino-1-oxobutyl]-N-trifluoroacetyl-L-serine.

NMR (D₂O) δ 1.42 (3H, d, J=3Hz), 2.07 (3H, s), 3.95 (1H, d, J=2Hz), 4.41 (1H, d, J=1Hz), 4.45 to 4.75 (2H, m), 5.48 (1H, dq, J=1 and 3Hz)

PREPARATION 23

Benzyl N-trifluoroacetyl-L-threonate

To a solution of benzyl L-threonate hydrochloride (10 g) and triethylamine (12.48 ml) in methanol (100 ml) was added methyl trifluoroacetate (8.2 ml) at room temperature. After stirring for an hour at room temperature, the reaction mixture was concentrated. The residue was diluted with ethyl acetate and washed successively with aqueous hydrogen chloride, water, 10% aqueous sodium hydrogen carbonate and brine. After drying over sodium sulfate, the ethyl acetate extract was concentrated. The residual crystals were washed with hexane to give benzyl N-trifluoroacetyl-L-threonate (10.68 g).

NMR (CDCl₃) δ 1.23 (3H, d, J=3Hz), 4.48 (1H, dq, J=1 and 3Hz), 4.64 (1H, dd, J=1 and 4Hz), 5.23 (2H, ABq, J=5 and 7Hz), 7.3 to 7.5 (5H, m)

PREPARATION 24

Benzyl O-(O-benzyl-N-benzyloxycarbonyl-L-threonyl)-N-trifluoroacetyl-L-threonate To a solution of O-benzyl-N-benzyloxycarbonyl-L-threonine (888 mg) and benzyl N-trifluoroacetyl-L-threonate (1 g) in methylene chloride (20 ml) was added N,N-diethylaminopropyl-N'-ethylcarbodiimide hydrochloride (558 mg) and 4-N,N-dimethylaminopyridine (36 mg) at room temperature. After stirring for 2 hours at room temperature, the reaction mixture was diluted with methylene chloride (80 ml) and washed successively with aqueous hydrogen chloride, water, 10% aqueous sodium hydrogen carbonate and brine. After drying over sodium sulfate, the methylene chloride extract was filtered and concentrated. The residue was chromatographed on silica gel (20 g) eluting successively with a 1:1 mixture of methylene chloride and hexane and methylene chloride to give benzyl O-(O-benzyl-N-benzyloxycarbonyl-L-threonyl)-N-trifluoroacetate-L-threonate (1.25 g).

NMR (CDCl₃) δ 1.20 (3H, d, J=3Hz), 1.27 (3H, d, J=3Hz), 4.04 (1H, dq, J=1 and 3Hz), 4.25 (1H, dd, J=1 and 4 Hz), 4.46 (2H, ABq, J=6 and 20Hz), 4.80 (1H, dd, J=1 and 4HZ), 5.0 to 5.6 (5H, m), 7.2 to 7.4 (15H, m)

PREPARATION 25

4-Methoxycarbonyl-5-trifluoromethyl-2-oxazoline

To a solution of methyl isocyanoacetate (4.55 ml) and triethylamine (7.0 ml) in benzene (45 ml) was added trifluoroacetaldehyde ethyl hemiacetal (8 ml) at 0° C. The mixture was stirred at room temperature for an hour and then heated with reflux for 2 hours. The resulting mixture was neutrized with acetic acid, evaporated, diluted with ethyl acetate and washed successively with water (2 times), 10% aqueous sodium hydrogen carbonate and brine. After drying over sodium sulfate, the ethyl acetate extract was filtered and concentrated. The residue was distilled (60° C. /4 mmHg) to give 4-methoxycarbonyl-5-trifluoromethyl-2-oxazoline (5 g).

NMR (CDCl$_3$) δ 3.85 (3H, s), 4.83 (1H, dd, J=1 and 2Hz), 5.12 (1H, dq, J=2 and 3Hz), 6.96 (1H, d, J=1Hz)

PREPARATION 26

2-(N-tert-Butyloxycarbonylamino)-3-hydroxy-4,4,4-trifluorobutylic acid

A solution of 4-methoxycarbonyl-5-trifluoromethyl-2oxazoline (10 g) in 6N aqueous hydrogen chloride (100 ml) was heated with reflux for 4 hours. The solvent was distilled off and the residue was also diluted with water and evaporated (2 times). The residue was dissolved in water (100 ml) and 4N aqueous sodium hydroxide (255 ml) and di-tert-butyl dicarbonate (12 ml) were added at room temperature and stirred for 2 hours at room temperature. The reaction mixture was washed successively with ethyl acetate and acidified with citric acid to pH 4 and extracted with ethyl acetate (2 times). The ethyl acetate extracts were combined and washed with brine. After drying over sodium sulfate, the ethyl acetate extract was filtered and concentrated to give 2-(N-tert-butoxycarbonylamino)-3-hydroxy-4,4,4-triflurorobutylic acid (5 g).

NMR (CD$_3$OD) δ 1.45 (9H, s), 4.48 (1H, d, J=1Hz), 4.56 (dq, 1H, J=1 and 4Hz)

PREPARATION 27

Benzyl O-[2-(N-tert-butoxycarbonylamino)-4,4,4-trifluoro-1-oxo-2-butenyl]-N-trifluoroacetyl-L-serinate To a solution of 2-(N-tert-butoxycarbonylamino)-hydroxy-4,4,4-trifluorobutylic acid (5 g), benzyl N-trifluoroacetyl-L-serinate (5.33 g) and -N,N-dimethylaminopyridine (224 mg) in methylene chloride (30 ml) was added N,N-dimethylaminopropyl-N'-ethylcarbodiimide hydrochloride (7.02 g) at room temperature. After stirring at room temperature overnight, the reaction mixture was washed successively with aqueous citric acid and brine. After drying over sodium sulfate, the methylene chloride extract was filtered and concentrated. The residue was chromatographed on silica gel (100 g) eluting successively with methylene chloride and a 4 1 mixture of methylene chloride and acetone to give benzyl -[2-(N-tert-butoxycarbonylamino)-4,4,4-trifluoro-1-oxo-butenyl]-N-trifluoroacetyl-L-serinate (2.87 g).

NMR (CDCl$_3$) δ 1.48 (9H, s), 4.52 (1H, dd, J=1 and 3Hz), 5.00 (2H, m), 5.25 (2H, ABq, J=3 and 8Hz), 5.46 (1H, q, J=3Hz), 7.3 to 7.5 (5H, m)

PREPARATION 28

O-(2-Amino-4,4,4-trifluoro-1-oxobutyl)-N-trifluoroacetyl-L-serine trifluoroactate A mixture of benzyl O-[2-(N-tert-butoxycarbonylamino)-4,4,4-trifluoro-1-oxo-2-butenyl]-N-trifluoroacetyl-L-serinate (2.67 g) and 10% palladium on activated carbon (1.3 g) in acetic acid (130 ml) was hydrogenated under hydrogen at 40 psi for an hour at room temperature. The reaction mixture was filtrated with Celite (filter aid, trade mark, made by Nakarai Chemicals) and concentrated and the residue was lyophilized. The residue was dissolved in trifluoroacetic acid (10 ml) at room temperature and the resulting solution was stirred for 30 minutes. The solvent was distilled off and the residue was lyophilized to give O-(2-amino-4,4,4-trifluoro-1-oxobutyl)-N-trifluoroacetyl-L-serine (1.82 g).

NMR (D$_2$O) δ 2.8 to 3.2 (2H, m), 4.5 to 4.8 (4H, m)
Mass m/e M+1 341

PREPARATION 29

Methyl 2-(N-benzyloxycarbonylamino)-3-hydroxy-4,4,4-trifluorobutyrate

A solution of 4-methoxycarbonyl-5-trifluoromethyl-2-oxazoline (5 g) in methanol (40.1) and conc. hydrogen chloride (10 ml) was heated at 50° C. for 4 hours. The reaction mixture was evaporated in vacuo and the residue was diluted with water (130 ml) and ethyl acetate (130 ml). To the mixture was added sodium hydrogen carbonate (12.8 g) and then benzyloxycarbonyl chloride (3.98 ml) at room temperature. The mixture was stirred for 2 hours at room temperature. The separated ethyl acetate layer was acidified with 6N aqueous hydrogen chloride to pH 2. The ethyl acetate extract was washed successively with 10% aqueous sodium hydrogen carbonate and brine. After drying over sodium sulfate, the ethyl acetate extract was filtered and concentrated. The precipitate was washed with a mixture of diisopropylether and hexane to give methyl 2-(N-benzyloxycarbonylamino)-3-hydroxy-4,4,4-trifluorobutyrate (3.3 g).

NMR (CDCl$_3$) δ 3.82 (3H, s), 4.58 (1H, dq, J=1 and 3 HZ), 4.78 (1H, dd, J=1 and 3 Hz), 5.15 (2H, s), 5.55 (1H, broad d, J=3Hz), 7.3 to 7.5 (5H, m)

PREPARATION 30

2-(N-Benzyloxycarbonylamino)-3-(2-tetrahydropyranyloxy)-4,4,4,-trifluorobutylic acid To a solution of methyl 2-(N-benzyloxycarbonylamino)3-hydroxy-4,4,4-trifluorobutyrate (3.3 g) in methylene chloride (33 ml) was added dihydropyran (1.1 ml) and pyridinium p-toluenesulfonate (251 mg) at room temperature. After stirring for 2 hours at room temperature, the solvent was distilled off and the residue was diluted with ethyl acetate, washed successively with aqueous sodium hydrogen carbonate and brine. After drying over sodium sulfate, the ethyl acetate was evaporated and the residue was diluted with methanol (20 ml). To the methanol solution was added 1N sodium hydroxide (10 ml) and the mixture was stirred for 2 hours at room temperature. The solvent distilled off and the residue was washed with ethyl acetate. The aqueous layer was acidified with citric acid to pH 4 and extracted with ethyl acetate (2 times). The combined ethyl acetate extracts were washed with brine, dried over sodium sulfate, filtered and concentrated. The residue was crystallized with a mixture of diisopropylether and hexane to give 2-(N-benzyloxycarbonylamino)-3-(2-tetrahydropyranyloxy)- 4,4,4,-trifluorobutyric acid (1 g).

NMR (CDCl$_3$) δ 1.3 to 1.9 (6H, m), 3.4 to 3.9 (2H, m), 4.6 to 4.9 (2H, m), 5.18 (2H, s), 5.62 (1H, dd, J=4 and 7Hz), 7.25 to 7.45 (5H, m)

PREPARATION 31

Benzyl N-trifluoroacetyl-O-[2-benzyloxycarbonylamino-3-(2-tetrahydropyranyloxy)-4,4,4-trifluoro-1-oxobutyl]-L-serinate To a solution of 2-(N-benzyloxycarbonylamino)3-(2-tetrahydropyranyloxy)-4,4,4-trifluorobutylic acid (1 g), benzyl N-trifluoroacetyl-L-serinate (746 mg) and 4-N,N-dimethylaminopyridine (31.3 μg) in methylene chloride (10 ml) was added N,N-diethylaminopropyl-N-ethylcarbodiimide hydrochloride (491 mg) at 0° C. The reaction mixture was allowed to warm to room temperature and stirred at room temperature for 2 hours. The reaction mixture was washed successively with citric acid, 10% aqueous sodium hydrogen carbonate and brine. After drying over sodium sulfate, the ethylacetate extract was filtered and concentrated. The residue was chromatographed on silica gel eluting successively with a mixture of methylene chloride and hexane (1:1) and methylene chloride to give benzyl N-trifluoroacetyl-O-[2-benzyloxycarbonylamino-3-(2-tetrahydropyranyloxy)-4,4,4-trifluoro-1-oxobutyl]-L-serinate (1.36 g).

NMR (CDCl$_3$) δ 1.4 to 1.8 (6H, m), 3.3 to 3.9 (2H, m), 4.3 to 5.0 (5H, m), 5.15 (2H, s 5.50 (1H, dd, J=4 and 7Hz), 7.2 to 7.5 (10H, m), 7.7 (1H, broad d, J=4Hz), 8.22 (1H, broad d, J=4Hz)

EXAMPLE 32

O-(2-Amino-3-hydroxy-4,4,4-trifluoro-1-oxobutyl)-N-trifluoroacetyl-L-serine

A solution of benzyl N-trifluoroacetyl-O-[2-benzyloxycarbonylamino-3-(2-tetrahydropyranyloxy)-4,4,4-trifluoro-1-oxobutyl]-L-serine (1.36 g) and p-toluenesulfonic acid monohydrate (39 mg) in methanol (14 ml) was stirred overnight. The solvent was distilled off and the residue was diluted with ethyl acetate and washed successively with 10% aqueous sodium hydrogen carbonate and brine. After drying over sodium sulfate, the ethyl acetate extract was filtered and concentrated. The residue was dissolved in acetic acid (50 ml) and 10% palladium on activated carbon (500 mg) was added. The mixture was hydrogenated under hydrogen at 40 psi at room temperature for an hour. The solvent was distilled off and the residue was lyophilized to give O-(2-amino-3-hydroxy-4,4,4-trifluoro-1-oxobutyl)-N-trifluoroacetyl-L-serine (685 mg).

NMR (D$_2$O) δ 4.6 to 4.8 (4H, m), 4.91 (1H, dq, J=1 and 4 Hz)

Mass m/e M+1 357

EXAMPLE 1

Fermentation

A culture medium (100 ml) containing corn starch (1%), glycerin (1%), glucose (0.5%), pharmamedia (0.5%), dried yeast. (0.5%), corn steep liquor (0.5%) and calcium carbonate (0.2%) (adjusted to pH 6.5) was poured into each of 500 ml Erlenmeyer flasks and sterilized at 120° C. for 30 minutes. A loopful of slant culture of Streptomyces sp. No. 8727 was inoculated to each of the media and cultured at 30° C. for 3 days on a rotary shaker. The resultant culture was inoculated to a medium containing soluble starch (2%), corn starch (1%), pharmamedia (1%), corn steep liquor (0.5%), dried yeast (0.1%), NaCl (0.1%), MgSO$_4$.7H$_2$O (0.05%), CaCO$_3$ (0.2%), Adekanol (deforming agent, trade mark, made by Asahi Denka Kogyo Co.) (0.1%) (150 liters) in a 200-liter jar-fermentor, which has been sterilized at 120° C. for 30 minutes in advance, and cultured at 30° C. for 4 days under aeration of 100 liters/minutes and agitation of 200 rpm.

Isolation and purification:

The culture broth thus obtained was filtered with an aid of diatomaseous earth (5 kg). The filtrate (110 liters) was adjusted to pH 7 and passed through a column of active carbon (10 liters, 20×32 cm). After washing with water (30 liters), elution was carried out with aqueous acetone (5%, 30 liters). The eluent was evaporated under reduced pressure to give an oily residue. The oily residue was mixed with 500 g of silica gel (Kiesel gel 60, 70-230 mesh, made by Merck Co., Ltd.), and this mixture was slurried in methanol. After evaporating the solvent, the resultant dry powder was subjected to column chromatography of the same silica gel (1.5 liter, 11×16 cm) which was packed with a mixture of chloroform, methanol and water (10:6:1 v/v). The column was developed with the same solvent system. Fractions containing the object compound were collected and concentrated under reduced pressure to give FR-900840 substance in the form of pale yellowish oil. This oil was dissolved in ethanol and concentrated under reduced pressure. This concentrate was kept at room temperature and purified FR-900840 substance (15 g) was obtained as pale yellowish crystals.

EXAMPLE 2

O-[2-Diazo-3(R)-hydroxy-1-oxobutyl]-N-trifluoroacetyl-L-serine

To a solution of O-(L-threonyl)-N-(trifluoroacetyl)-L-serine (109 mg) were added aqueous 4M chloroacetic acid (20 μl) and aqueous 6M potassium nitrite (120 μl) and the solution was stirred at room temperature for 15 minutes.

EXAMPLE 3

FR-900840 substance
[0-[2-diazo-3(R)-hydroxy-1-oxobutyl]-L-serine]

Acylase I (acylase, Sigma A-7264, made by Sigma Chemicals) (20 mg) was added to the mixture and the pH of the mixture was maintained between 7.0 and 7.3 with the addition of pH 8 2M Tris buffer. After stirring for 120 minutes at room temperature, the mixture was lyophilized and the residue was adsorbed on a charcoal column. The column was washed with water and then eluted with acetone-H$_2$O (5:95) and the eluent was evaporated to dryness. The obtaihed residue was purified by chromatography on silica gel column (CHCl$_3$-methanol-H$_2$O) (5:3:1) to afford O-[2-diazo-3(R)-hydroxy-1-oxobutyl]-L-serine (20 mg), which is identical with F.R-900840 substance prepared by fermentation process described in all respects.

IR (Nujol) 3420, 3270, 3100, 2920, 2250, 2100, 1660, 1610, 1560, 1520, 1460, 1410, 1380, 1350, 1290, 1230, 1160, 1140, 1090, 1070, 1010, 960, 900, 840, 820, 790, 740, 705 cm$^{-1}$ NMR (D₂O) δ 4.86 (1H, q, J=6.6Hz), 4.62 (2H, d, J=3.8Hz), 4.10 (1H, t, J=3.8Hz), 1.42 (3H, d, J=6.6Hz)

FAB-MS m/z 218 (M+H)

EXAMPLE 4

O-[2-Diazo-3(S)-hydroxy-1-oxobutyl]-L-serine

To a solution of O-(R-threonyl)-N-trifluoroacetyl-L-serine (400 mg) and 4M aqueous chloroacetic acid (40 ml) in water was added sodium nitrite (183 mg) at room temperature. After stirring for 15 minutes at room temperature, the reaction mixture was neutrized with 2M tris buffer solution to pH 7.0 to 7.3 and Acylase I (acylase, Sigma A-7264, made by Sigma Chemicals) (40 mg) was added at room temperature. After stirring for 5 hours at room temperature, the reaction mixture was chromatographed on carbon eluting successively with water and a 9:1 mixture of water and acetone and then on silica gel eluting successively with 10:6:1 mixture of chloroform, methanol and water, and lyophilized to give O-[2-diazo-3(S)-hydroxy-1-oxobutyl]-L-serine.

NMR (D₂O) δ 1.42 (3H, d, J=6Hz), 4.1 (1H, t, J=5Hz), 4.5 to 4.7 (2H, m), 4.9 (1H, q, J=6Hz)

IR (KBr) 3300, 2100, 1620, 1290 cm⁻¹

EXAMPLE 5

O-(2-Diazo-3-hydroxy-3-phenyl-1-oxobutyl)-L-serine

To a solution of O-(D,L-phenylserinyl)-N-trifluoroacetyl-L-serine (150 mg) and 4M aqueous chloroacetic acid (40 μl) in water (5 ml) was added sodium nitrite (60 mg) at room temperature. After stirring for 30 minutes at room temperature, the reaction mixture was neutrized with 2M tris buffer solution to pH 7.0 to 7.3 and Acylase I (acylase, Sigma A-7264, made by Sigma Chemicals) (45 mg) was added. After stirring for 6 hours at room temperature, the reaction mixture was chromatographed on carbon eluting successively with water and 95:1 mixture of water and acetone and then silica gel eluting with 10:6:1 mixture of chloroform, methanol and water, and then lyophilized to give O-(2-diazo-3-hydroxy-3-phenyl-1-oxobutyl)-L-serine (15 mg).

NMR (D₂O) δ 4.5 to 4.8 (3H, m), 5.8 to 5.9 (1H, m), 7.3 to 8.0 (5H, m)

EXAMPLE 6

O-(2-Diazo-3-hydroxy-1-oxopropyl)-L-serine

To a solution of O-(L-serinyl)-N-trifluoroacetyl-L-serine (400 mg) and 4M aqueous chloroacetic acid (50 μl) is water (4 ml) was added sodium nitrite (193 mg) at room temperature. After stirring for 15 minutes at room temperature, the reaction mixture was neutrized with 2M tris buffer solution to pH 7.0 to 7.3 and then Acylase I (acylase, Sigma A-7264, made by Sigma Chemicals) (60 mg) was added. The mixture was stirred for 5 hours at room temperature, and chromatographed on carbon (50 ml) eluting successively with water and a 9:1 mixture of water and acetone to give a crude product, which was chromatographed on silica gel eluting with a mixture of methylene chloride, methanol and water (10:6:1 to 5:3:1), and also chromatographed on silica gel eluting with a 5:3:1 mixture of methylene chloride, methanol and water (5:3:1) to give a pure product which was lyophylized to give O-(2-diazo-3-hydroxy-1-oxopropyl)-L-serine (33 mg).

NMR (D₂O) δ 4.05 (1H, t, J=3.6Hz), 4.45 (2H, s), 4.60 (2H, m)

EXAMPLE 7

Ethyl 2-diazo-3(R)-hydroxybutyrate

To a solution of ethyl L-threonate (50 mg) and 4M aqueous chloroacetic acid (60 μl) in water (1 ml) was added sodium nitrite (46.9 mg) at room temperature. After stirring for 5 minutes at room temperature, the reation mixture was extracted with ethyl acetate. After drying over sodium sulfate, the ethyl acetate extract was filtered and concentrated. The residue was chromatographed on preparative thin layer chromatography to give ethyl 2-diazo-3(R)-hydroxybutyrate (8 mg).

NMR (CDCl₃) δ 1.29 (3H, t, J=8Hz), 1.40 (3H, d, J=6Hz), 4.26 (2H, q, J=8Hz), 4.95 (1H, q, J=6Hz)

IR (neat) 3450, 3000, 2125, 1750, 1695, 1300 cm⁻¹

EXAMPLE 8

O-(2-Diazo-1,3-dioxobutyl)-N-trifluoroacetyl-L-serine

To a solution of O-acetoacetyl-N-trifluoroacetyl-L-serine (232 mg) and triethylamine (0.41 ml) in ethanol (7 ml) was added p-toluenesulfonyl azide (193 mg) at 0° C. The mixture was stirred for an hour at 0° C. and for 4 hours at room temperature. The solvent was distilled off in vacuo and the residue was diluted with chloroform and washed successively with aqueous acetic acid, water and brine. After drying over sodium sulfate, the chloroform extract was filtered and concentrated. The residue was flash chromatographed on silica gel (10 g) eluting successively with chloroform and a 1:9 mixture of methanol and chloroform to give O-(2-diazo-1,3-dioxobutyl)-N-trifloroacetyl-L-serine (193 mg).

NMR (D₂O) δ 2.33(3H, s), 4.31 (1H, dd, J=3 and 4Hz), 4.51 (1H, dd, J=2 and 3Hz), 4.70 (1H, dd, J=2 and 4Hz)

EXAMPLE 9

O-(2-Diazo-1,3-dioxobutyl)-L-serine

A solution of O-(2-diazo-1,3-dioxobutyl)-N-trifluoroacetyl-L-serine (193 mg) and Acylase I (acylase, Sigma A-7264, made by Sigma Chemicals) (60 mg) in water (6 ml) was neutrized to pH 7.0–7.3 with 2M tris buffer solution and the mixture was stirred for 4 hours at 40° C. The reaction mixture was chromatographed on carbon (20 ml) eluting successively with water, a 1:1 mixture of acetone and water and acetone to give a crude solid (100 mg). The above solid (50 mg) was chromatographed on silica gel (2.5 g) eluting successively with a 9:1 mixture of chloroform and methanol and a 65:25:4 mixture of chloroform, methanol and water to give O-(2-diazo-1,3-dioxobutyl)-L-serine (22 mg).

NMR (D₂O) δ 2.45 (3H, s), 4.13 (1H, t, J=2Hz), 4.68 (2H, d, J=2Hz)

IR (Nujol) 2140 and 1720 cm⁻¹

Mass (M+1) 216

EXAMPLE 10

2-Carboxyethyl 2-diazo-3(R)-hydroxybutyrate

To a solution of 2-carboxyethyl L-threonate (220 mg) and 4M aqueous chloroacetic acid (25 μl) in water (5 ml) was added sodium nitrite (159 mg) at room temperature. After stirring for 10 minutes at room temperature, the reaction mixture was neutrized with 2M tris buffer solution to pH 7.0 and chromatographed on carbon (25 ml) eluting successively with water and a 9:1 mixture of water and acetone to give a crude product, which was also chromatographed on silica gel eluting with a 5:3:1 mixture of chloroform, methanol and water, and lyophylized to give 2-carboxyethyl 2-diazo-3(R)-hydroxybutyrate (60 mg).

NMR (D$_2$O) δ 1.39 (3H, d, J=6Hz), 2.65 (2H, t, J=7Hz), 4.40 (2H, t, J=5Hz), 4.85 (1H, q, J=6Hz)

IR (neat) 3350, 2970, 2100, 1680 cm$^{-1}$

EXAMPLE 11

2-Trifluoroacetamidoethyl 2-diazo-3(R)-hydroxybutyrate

To a solution 2-trifluoroacetamidoethyl L-threonate (1g) and 4M aqueous chloroacetic acid (0.1 ml) in water (20 ml) was added sodium nitrite (534 mg) at room temperature. The reaction mixture was stirred for 30 minutes at room temperature and 10% aqueous sodium hydrogen carbonate was added to it. The resulting mixture was extracted with ethyl acetate (2 times) and the combined ethyl acetate extracts were washed with brine and dried over sodium sulfate and filtered. The solvent was distilled off and the residue was chromatographed on silica gel (20 g) eluting successively with methylene chloride and a 24:1 mixture of methylene chloride and acetone to give 2-trifluoroacetamidoethyl 2-diazo-3(R)-hydroxybutyrate (200 mg).

NMR (D$_2$O) δ 1.43 (d, 3H, J=3Hz), 3.60 to 3.72 (2H, m), 4.25 to 4.55 (2H, m), 4.93 (1H, q, J=3Hz)

IR (Nujol) 2100, 1710 cm$^{-1}$

EXAMPLE 12

O-[2-Diazo-3(R)-hydroxy-1-oxobutyl]-L-homoserine

To a solution of O-L-threonyl-N-trifluoroacetyl-L-homoserine (800 mg) and 4M aqueous chloroacetic acid (100 μl) in water (10 ml) was added sodium nitrite (345 mg) at room temperature. After stirring for 15 minutes at room temperature, the reaction mixture was neutrized with 2M tris buffer solution to pH 7.0 to 7.3 and then Acylase I (acylase, Sigma A-7264, made by Sigma Chemicals) (100 mg) was added. The mixture was stirred for 5 hours at 35° C. and chromatographed on carbon (50 ml) eluting successively with water and a 9:1 mixture of water and acetone to give O-[2-diazo-3(R)-hydroxy-1-oxobutyl]-L-homoserine (28 mg).

NMR (D$_2$O) δ 1.45 (3H, d, J=7Hz), 3.82 (1H, t, J=5.5Hz), 4.38 (2H, m), 4.90(1H, q, J=7Hz)

IR (KBr) 3300, 2080, 1600, 1280 cm$^{-1}$

EXAMPLE 13

O-[3(R)-Acetoxy-2-diazo-1-oxobutyl]-N-trifluoroacetyl-L-serine

To a mixture of O-[3(R)-acetoxy-2(S)-amino-1-oxobutyl]-N-trifluoroacetyl-L-serine (200 mg) and chloroacetic acid (0.015 ml) in water (2ml) was added sodium nitrite (80 mg) at room temperature. After stirring for 0.5 hour at room temperature, acetic acid was added and the mixture was extracted with ethyl acetate (3 times) and the ethyl acetate extracts were combined and washed with brine. After drying over sodium sulfate, the ethyl acetate extract was filtered and concentrated. The residue was chromatographed on preparative thin layer chromatography to give O-[3(R)-acetoxy-2-diazo-1-oxobutyl]-N-trifluoroacetyl-L-serine (8 mg).

NMR (D$_2$O) δ 1.52 (3H, d, J=3Hz), 2.46 (3H, s), 4.4 to 4.8 (3H, m), 4.90 (1H, q, J=3Hz)

EXAMPLE 14

O-(2-Diazo-3(R)-hydroxy-1-oxobutyl)-N-trifluoroacetyl-L-threonine

A mixture of benzyl O-(O-benzyl-N-benzyloxycarbonyl L-threonyl)-N-trifluoroacetyl-L-threonate (1.25 g) and 10% palladium on activated carbon (600 mg) in acetic acid (600 ml) was hydrogenated under hydrogen at 40 psi at room temperature for 4 hours. The solvent was distilled off and the residue was diluted with water and lyophilized to give a white solid (605 mg). The white solid (605 mg) was dissolved in water (6 ml) and sodium nitrite (273 mg) was added to it at room temperature. After stirring for half an hour at room temperature, the reaction mixture was chromatographed on carbon (60 ml) eluting successively with water and a 1:9 mixture of acetone and water to give a crude product, which was chromatographed on preparative thin layer chromatography eluting with a 65:25:4 mixture of chloroform, methanol and water to give O-(2-diazo-3(R)-hydroxy-1-oxobutyl)-N-trifluoroacetyl-L-threonine (120 mg).

NMR (D$_2$O) δ 1.37 (3H, d, J=3Hz), 1.42 (3H, d, J=3Hz), 4.50 (1H, d, J=2Hz), 4.85 (1H, q, J=3Hz), 5.49 (1H, dq, J=2 and 3Hz)

EXAMPLE 15

O-(2-Diazo-4,4,4-trifluoro-1-oxobutyl)-N-trifluoroacetyl-L-serine

To a solution of O-(2-amino-4,4,4-trifluoro-1-oxobutyl)-N-trifluoroacetyl-L-serine (88 mg) in water (3 ml) was added sodium nitrite (25.3 mg) at room temperature. After stirring for 30 minutes at room temperature, the reaction mixture was neutrized with 2M tris buffer solution to pH 7.0 to 7.3. The mixture was chromatographed on carbon (10 ml) eluting with water and then a 9:1 mixture of water and acetone to give a crude product, which was also chromatographed on preparative thin layer chromatography to give O-(2-diazo-4,4,4-trifluoro-1-oxobutyl)-N-trifluoroacetyl-1-serine (15 mg).

NMR (D$_2$O) δ 3.26 (2H, q, J=11Hz), 4.4 to 4.55 (1H, m), 4.6 to 4.75 (2H, m)

IR (Nujol) 2110, 1700 cm$^{-1}$

EXAMPLE 16

O-(2-Diazo-4,4,4-trifluoro-1-oxobutyl)-L-serine

To a solution of O-(2-amino-4,4,4-trifluoro-1-oxobutyl)-N-trifluoroacetyl-L-serine trifluoroacetate (500 mg) in water (5 ml) was added sodium nitrite (146 mg) at room temperature. After stirring for 30 minutes at room temperature, the reaction mixture was neutrized with 2M tris buffer solution to pH 7.0 to 7.3 and Acylase I (acylase, Sigma A-7264, made by Sigma Chemicals) (70 mg) was added. After stirring for 6 hours at room temperature, the mixture was chromatographed on SP (trade mark, made by MITSUBISHI CHEMICAL INDUSTRIES LTD.) (50 ml) eluting successively with water and a 9:1 mixture of water and acetone to give a crude product, which was chromatographed on preparative thin layer chromatography eluting with a 65:25:4 mixture of chloroform, methanol and water to give O-(2-diazo-4,4,4-trifluoro-1-oxobutyl)-L-serine (28 mg).

NMR (D$_2$O) δ 4.08 (1H, t, J=2Hz), 4.64 (2H, d, J=2Hz), 5.18 (1H, q, J=4Hz)

IR (Nujol) 2160, 1700 cm$^{-1}$

EXAMPLE 17

O-(2-Diazo-3-hydroxy-4,4,4-trifluoro-1-oxobutyl)-L-serine

To a solution of O-(2-amino-3-hydroxy-4,4,4-trifluoro-1-oxobutyl)-N-trifluoroacetyl-L-serine (685 mg) and chloroacetic acid (0.04 ml) in water (7 ml) was added sodium nitrite (227 mg) at room temperature. After stirring for 30 minutes at room temperature, the reaction mixture was neutrized with 2M tris buffer solution to pH 7.0 to 7.3 and then Acylase I (acylase, Sigma A-7264, made by Sigma Chemicals) (140 mg) was added. The mixture was stirred for 6 hours at room temperature and chromatographed on carbon (60 ml) eluting successively with water and a 9:1 mixture of water and acetone to give a crude product, which was chromatographed on preparative thin layer chromatography eluting with a 65:35:4 mixture of chloroform, methanol and water, and lyophilized to give O-(2-diazo-3-hydroxy-4,4,4-trifluoro-1-oxobutyl)-L-serine (113 mg).

NMR ($D_2O$) δ 4.10 (1H, t, J=2Hz), 4.65 (2H, d, J=2Hz), 5.18 (1H, q, J=3Hz)

IR (Nujol) 2130, 1690 $cm^{-1}$

What we claim is:

1. O-[2-Diazo-3(R)-hydroxy-1-oxobutyl]-L-serine.

* * * * *